United States Patent
Dai et al.

(10) Patent No.: US 10,699,412 B2
(45) Date of Patent: Jun. 30, 2020

(54) STRUCTURE CORRECTING ADVERSARIAL NETWORK FOR CHEST X-RAYS ORGAN SEGMENTATION

(71) Applicant: Petuum, Inc., Pittsburgh, PA (US)

(72) Inventors: Wei Dai, Pittsburgh, PA (US); Xiaodan Liang, Pittsburgh, PA (US); Hao Zhang, Pittsburgh, PA (US); Eric Xing, Pittsburgh, PA (US); Joseph Doyle, Marlton, NJ (US)

(73) Assignee: PETUUM INC., Pittsburgh, PA (US)

( * ) Notice: Subject to any disclaimer, the term of this patent is extended or adjusted under 35 U.S.C. 154(b) by 190 days.

(21) Appl. No.: 15/925,998

(22) Filed: Mar. 20, 2018

(65) Prior Publication Data
US 2018/0276825 A1    Sep. 27, 2018

Related U.S. Application Data (60) Provisional application No. 62/475,742, filed on Mar. 23, 2017.

(51) Int. Cl.
*G06K 9/00*    (2006.01)
*G06T 7/11*    (2017.01)
(Continued)

(52) U.S. Cl.
CPC .............. *G06T 7/11* (2017.01); *A61B 5/7267* (2013.01); *A61B 6/50* (2013.01); *A61B 6/5211* (2013.01); *G06K 9/628* (2013.01); *G06K 9/6227* (2013.01); *G06K 9/6298* (2013.01); *G06T 7/13* (2017.01); *G06T 7/143* (2017.01); *G06T 7/187* (2017.01); *G06K 2209/051* (2013.01); *G06T 2207/10116* (2013.01); *G06T 2207/20076* (2013.01); *G06T 2207/20081* (2013.01);
(Continued)

(58) Field of Classification Search
CPC . G06T 2207/30061; G06T 2207/10116; G06T 2207/20076; G06T 2207/20081; G06T 2207/20084; G06T 2207/30048; G06T 7/13; G06T 7/143; G06T 7/187; G06T 7/11; G06K 9/3233; G06K 9/6227; G06K 9/6232; G06K 9/628; G06K 9/6287; G06K 9/6298; G06K 2209/051; A61B 5/7267; A61B 6/50; A61B 6/5211; G06N 3/0454
See application file for complete search history.

(56) References Cited

U.S. PATENT DOCUMENTS

9,704,257 B1 * 7/2017 Tuzel ...................... G06N 3/04
2017/0169313 A1 * 6/2017 Choi ................... G06K 9/6267
(Continued)

*Primary Examiner* — Amara Abdi (57) ABSTRACT

Organ segmentation in chest X-rays using convolutional neural networks is disclosed. One embodiment provides a method to train a convolutional segmentation network with chest X-ray images to generate pixel-level predictions of target classes. Another embodiment will also train a critic network with an input mask, wherein the input mask is one of a segmentation network mask and a ground truth annotation, and outputting a probability that the input mask is the ground truth annotation instead of the prediction by the segmentation network, and to provide the probability output by the critic network to the segmentation network to guide the segmentation network to generate masks more consistent with learned higher-order structures.

6 Claims, 4 Drawing Sheets

(51) Int. Cl.
- *G06T 7/13* (2017.01)
- *G06T 7/187* (2017.01)
- *G06K 9/62* (2006.01)
- *A61B 5/00* (2006.01)
- *A61B 6/00* (2006.01)
- *G06T 7/143* (2017.01)

(52) U.S. Cl.
CPC ............... *G06T 2207/20084* (2013.01); *G06T 2207/30048* (2013.01); *G06T 2207/30061* (2013.01)

(56) References Cited

U.S. PATENT DOCUMENTS

2018/0218502 A1\* 8/2018 Golden .................... G06N 3/08
2019/0088359 A1\* 3/2019 Moore ................. G06K 9/6271

\* cited by examiner

STRUCTURE CORRECTING ADVERSARIAL NETWORK FOR CHEST X-RAYS ORGAN SEGMENTATION

CROSS REFERENCE TO RELATED APPLICATIONS

This application claims priority to prior filed provisional application Ser. No. 62/475,742 entitled "Scan: Structure Correcting Adversarial Network for Chest X-rays Organ Segmentation" filed on Mar. 23, 2017, the content of which is incorporated herein by reference in its entirety.

BACKGROUND

Field of the Invention

The invention relates generally to chest X-ray organ segmentation, and more specifically, is directed to a structure correcting neural network to effectively segment human physiology in chest X-rays while using relatively small training datasets.

Prior Art

Chest X-rays (CXR) are one of the most common medical imaging procedures with over 2-10 times more scans than other imaging modalities such as MRI, CT scan, and PET scans. In turn, the number of CXR scans places significant workloads on radiologists and medical practitioners.

In Chest X-rays, organ segmentation is a crucial step in determining lung physiology and pathologies. It is an important step in computer aided detection, diagnosis, surgery and treatment. Accurate segmentation of lung fields and the heart provide rich structure information about shape irregularities and size measurements that are useful to assess certain clinical conditions such as cardiomegaly, pneumothorax, pleural effusion, and emphysema, among others. Historically, organ segmentation has been hand annotated on chest X-rays by radiologists.

Using machine learning for organ segmentation is non-trivial. Computer-aided detection is challenging in X-rays due to the fact that X-rays are a 2-D projection of a 3-D structure, resulting in overlap between organ structures. Some current state-of-the-art approaches use the more brittle multi-stage processing that starts with similar patient lung profiles and then uses key point matching to perform linear deformations to fit the lung profile. Neural Network approaches have been applied to image-level computer-aided detection, but not pixel-level segmentation. Furthermore, those neural network approaches rely on large datasets and models, which are not readily available for segmentation.

SUMMARY

Accordingly, an improved method and apparatus for a structure correcting adversarial network for organ segmentation is described below in the Detailed Description. For example, one disclosed embodiment provides a method to train a convolutional segmentation network with chest X-ray images to generate pixel-level predictions of target classes. Another embodiment will also to train a critic network with an input mask, wherein the input mask is one of a segmentation network mask and a ground truth annotation, and outputting a probability that the input mask is the ground truth annotation instead of the prediction by the segmentation network, and to provide the probability output by the critic network to the segmentation network to guide the segmentation network to generate masks more consistent with learned higher-order structures.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The present disclosure, in accordance with one or more various embodiments, is described in detail with reference to the following figures. The drawings are provided for purposes of illustration only and merely depict exemplary embodiments of the disclosure. These drawings are provided to facilitate the reader's understanding of the disclosure and should not be considered limiting of the breadth, scope, or applicability of the disclosure. It should be noted that for clarity and ease of illustration these drawings are not necessarily made to scale.

DETAILED DESCRIPTION

The following description is presented to enable a person of ordinary skill in the art to make and use the invention. Descriptions of specific devices, techniques, and applications are provided only as examples. Various modifications to the examples described herein will be clear to those of ordinary skill in the art, and the general principles defined herein may be applied to other examples and applications without departing from the spirit and scope of the invention. Thus, embodiments of the present invention are not intended to be limited to the examples described herein and shown, but is to be accorded the scope consistent with the claims.

The word "exemplary" is used herein to mean "serving as an example or illustration." Any aspect or design described herein as "exemplary" is not necessarily to be construed as preferred or advantageous over other aspects or designs.

Reference will now be made in detail to aspects of the subject technology, examples of which are illustrated in the accompanying drawings, wherein like reference numerals refer to like elements throughout.

The specific order or hierarchy of steps in the processes disclosed herein is an example of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

A key step in computer-aided detection on chest X-ray ("CXR") images is organ segmentation. The segmentation of the lung fields and the heart provides rich structure information about shape irregularities and size measurements that can be used to directly assess certain serious clinical conditions, such as cardiomegaly (enlargement of the heart), pneumothorax (lung collapse), pleural effusion, and emphysema. Key clinical indicators such as cardiothoracic ratio (CTR) can be readily derived from organ segmentation. Furthermore, explicit lung region masks can also improve interpretability of computer-aided detection by localizing the diagnosis to relevant lung fields or heart, which is important for the clinical use.

Figure 1:
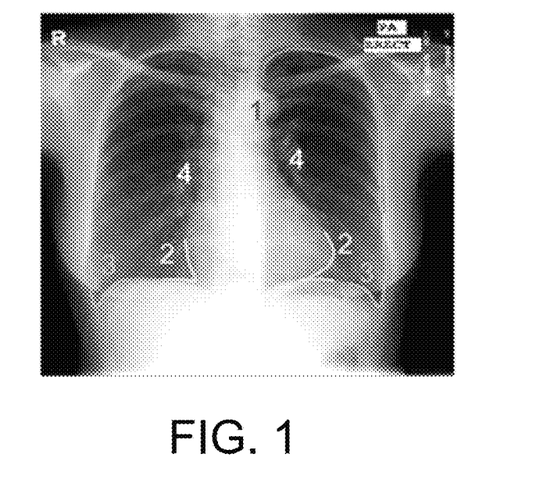
FIG. 1 is an X-ray image annotated to show important contour landmarks around lung fields.

One major challenge in CXR segmentation is to incorporate the implicit medical knowledge involved in contour determination. Basically, the positional relationship between the lung fields and the heart implies the adjacency of the lung and heart masks. Moreover, when medical experts annotate the lung fields, they look for certain consistent structures surrounding the lung fields, as shown in FIG. 1. Such prior knowledge helps resolve boundaries around less clear regions caused by pathological conditions or poor imaging quality.

Therefore, a successful segmentation model effectively leverages global structural information to resolve the local details. Unfortunately, unlike natural images, there is very limited CXR training data with pixel-level annotations, due to the expensive label acquisition involving medical professionals. Furthermore, CXRs exhibit substantial variations across different patient populations, pathological conditions, as well as imaging technology and operation. Finally, CxR images are gray-scale and are drastically different from natural images, which may limit the transferability of existing models. Existing approaches to CXR organ segmentation generally rely on hand-crafted features that can be brittle when applied on a different patient population, disease profiles, and image quality. Furthermore, these methods do not explicitly balance local information with global structure in a principled way, which is critical to achieve realistic segmentation outcomes suitable for diagnostic tasks.

Therefore, disclosed herein, some embodiments provide a method to train a convolutional segmentation network with chest X-ray images to generate pixel-level predictions of target classes. Also disclosed herein are embodiments that sue the convolutional segmentation network trained with chess X-ray images to generate pixel-level predictions of target classes further comprising a structure correcting adversarial network ("SCAN") incorporates a critic network to impose the structural regularities emerging from human physiology on a convolutional segmentation network. In some embodiments, organ segmentation may be used in medical imaging scans other than chest X-rays, for example, in medical images that have similar aspects such as two-dimensional projections of three-dimensional structures.

For example, during training, the critic network learns to discriminate between ground truth organ annotations from masks synthesized by the segmentation network. Through this adversarial process, the critic network learns higher order structures and guides the segmentation model to achieve realistic segmentation outcomes. Further, this approach is feasible with very limited training data available, and can reach human-level performance without relying on any existing trained model or dataset. We will now describe the embodiments in the figures.

FIG. 1 is an X-ray image annotated to show important contour landmarks around lung fields. Aortic arch 1 is excluded from lung fields in organ segmentation. Hila and other vascular structures 4 are considered part of the lung fields. In healthy patients, costophrenic angles 3, cardiodiaphragmatic angles 2 and the rib cage contour 5 should be visible in a chest X-ray. As can be seen, the overlapping and blurry nature of some lung fields and other organic structures are not readily ascertainable without considerable training over many input images.

Figure 2:
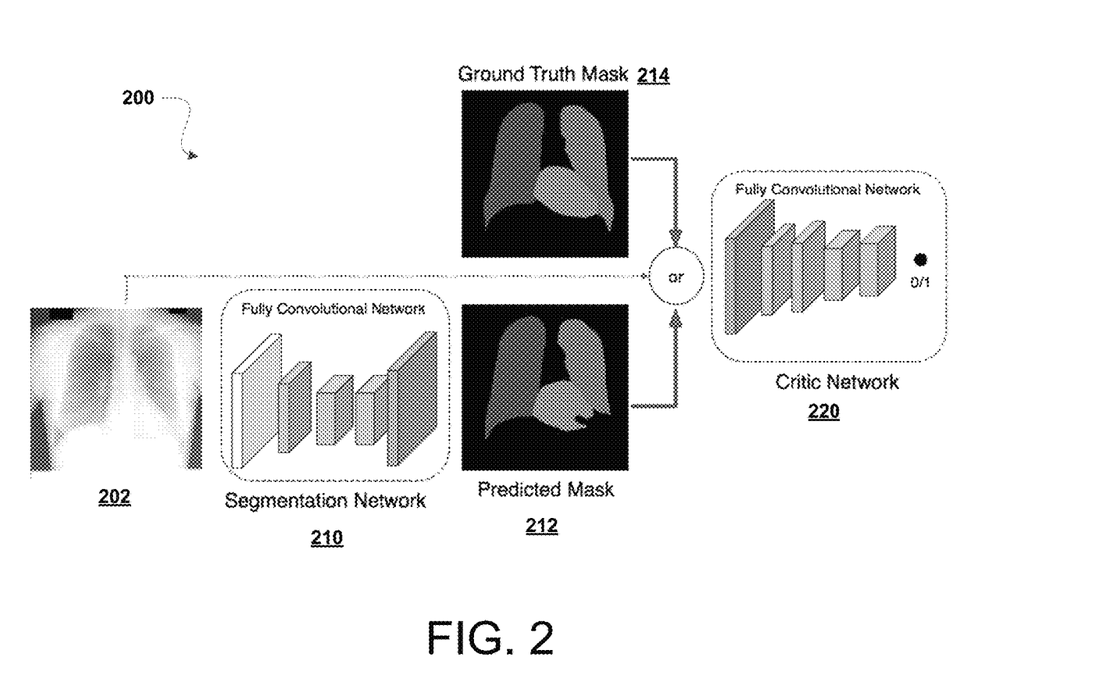
FIG. 2 illustrates an overview of one embodiment of a SCAN framework according to embodiments of the invention.

FIG. 2 illustrates an overview of one embodiment of a SCAN framework 200 that jointly trains a segmentation network 210 and a critic network 220 with an adversarial mechanism. In this example, the segmentation network 210 produces per-pixel class prediction 212 while the critic receives either a ground truth label 214 or the per-pixel class prediction 212 from the segmentation network 210, and outputs a probability estimate of whether the input is the ground truth 214 or the segmentation network prediction 212. In the illustrated embodiment, the critic network 220 may have a training target of 1 for the ground truth label and a training target of 0 for the segmentation network prediction. In some embodiments, critic network 220 may additionally receive chest X-ray image 202.

Figure 3:
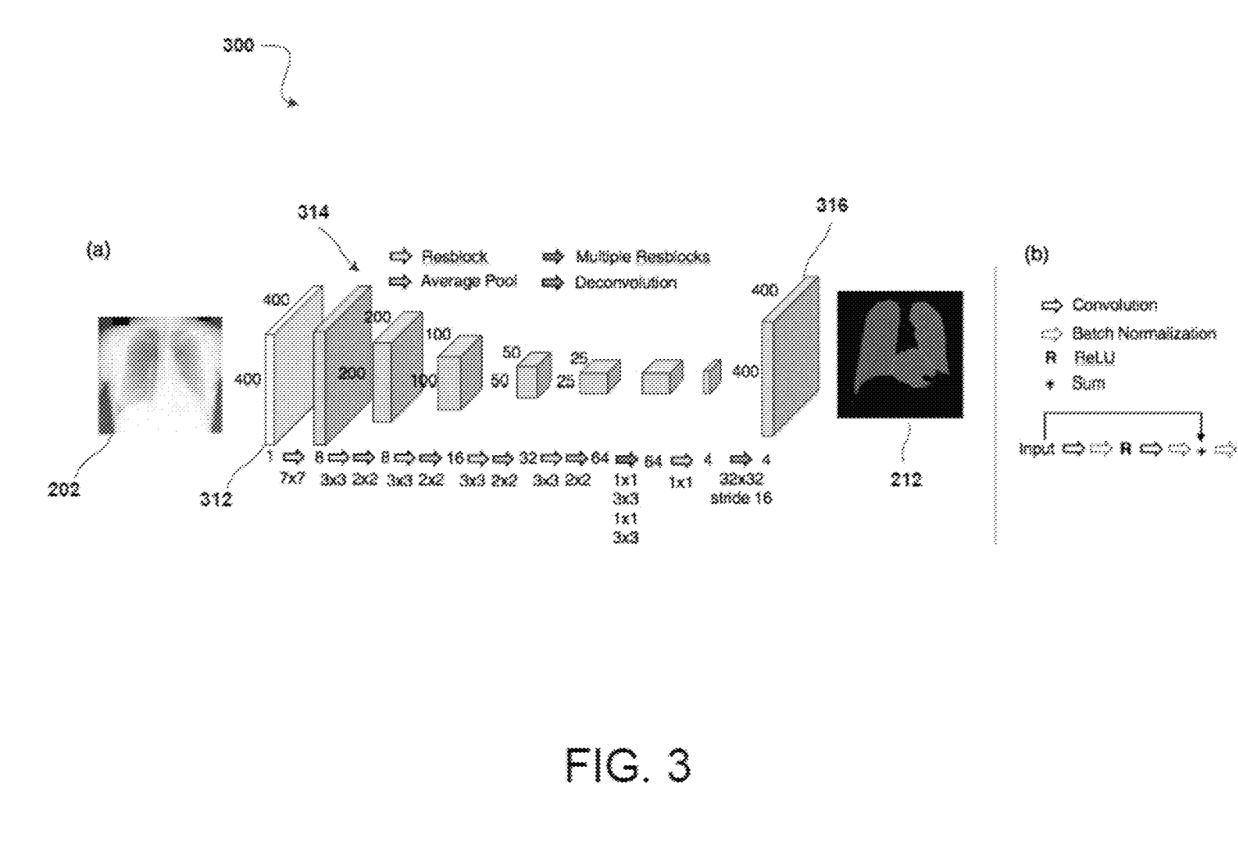
FIG. 3 illustrates an exemplary segmentation network architecture according to embodiments of the invention.
Figure 4:
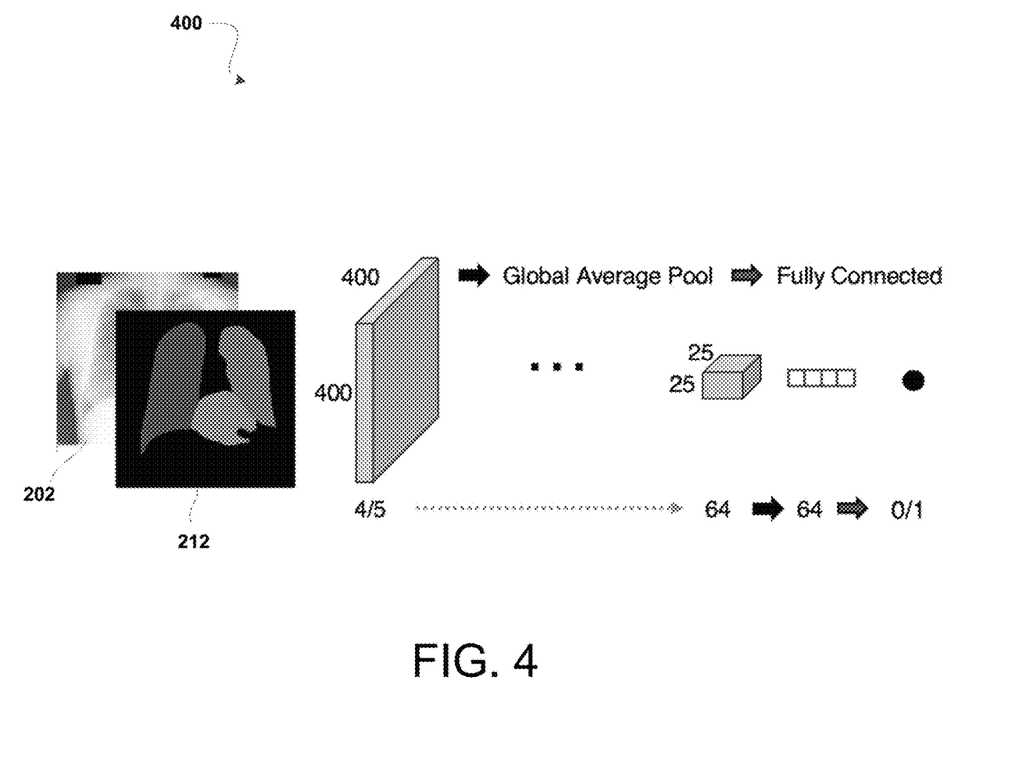
FIG. 4 illustrates an exemplary critic network architecture according to embodiments of the invention.

FIG. 3 illustrates one embodiment of a segmentation network architecture 300 and FIG. 4 illustrates a one embodiment of a critic network architecture 400 according to some embodiments of this disclosure. While these figures show specific details of the segmentation 300 and critic networks 400, other embodiments are not limited to the illustrated networks. Additionally, segmentation and critic network are each one example of the segmentation 210 and critic network 220 of FIG. 2, but are shown with additional detail. We now turn to describe technical aspects of these examples. For clarity, variables within the equations will primarily be referenced by their variable name to better associate them with the equation(s).

Let S, D be the segmentation network 300 and the critic network 400, respectively. The data consist of the input images 202, also $x_i$, and the associated mask labels 212 and 214, also $y_i$, where $x_i$ is of shape [H, W, 1] for a single-channel grayscale image with height H and width W, and $y_i$ is of shape [H, W, C] where C is the number of classes including the background. Note that for each pixel location (j, k), $y_i^{jkc}=1$ for the labeled class channel c while the rest of the channels are zero ($y_i^{ekc'}=0$ for c'≠c). We use $S(x)\in[0,1]^{[H,W,C]}$ to denote the class probabilities predicted by S at each pixel location such that the class probabilities normalize to 1 at each pixel. Let $D(x_i, y)$ be the scalar probability estimate of y coming from the training data (ground truth) $y_1$ instead of the predicted mask $S(x_i)$. We define the optimization problem as $$\min_S \max_D \left\{ J(S, D) := \sum_{i=1}^{N} J_s(S(x_i), y_i) - \lambda [J_d(D(x_i, y_i), 1) + J_d(D(x_i, S(x_i)), 0)] \right\}, \quad (1)$$

where is the multi-class cross-entropy loss for predicted mask ŷ averaged over all pixels. $J_a(\hat{t}, t):=-t\ln\hat{t}+(1-t)\ln(1-\hat{t})$ is the binary logistic loss for the critic's prediction. λ is a tuning parameter balancing pixel-wise loss and the adversarial loss. We can solve Eq. (1) by alternate between optimizing S and optimizing D using their respective loss functions.

Since the first term in Eq. (1) does not depend on D, we can train our critic network by minimizing the following objective with respect to D for a fixed S:

$\Sigma_{i=1}^{N} J_d(D(x_i, y_i), 1) + J_d(D(x_i, S(X_i)), 0)$

Given a fixed D, we train the segmentation network by minimizing the following objective with respect to S:

$$\sum_{i=1}^{N} J_s(S(x_i), y_i) + \lambda J_d(D(x_i, S(x_i)), 1)$$

Note that $J_d(D(x_i, S(x_i)), 1)$ is used in place of $-J_d(D(x_i, S(x_i)), 0)$. This is valid as they share the same set of critical points. The reason for this substitution is that $J_d(D(x_i, S(x_i)), 0)$ leads to weaker gradient signals when D makes accurate predictions, such as during the early stage of training.

In some embodiments, SCAN framework 200 may comprise a method including training a convolutional segmentation network with chest X-ray images 202 to generate pixel-level predictions 212 of target classes. In some embodiments, the target classes include classes for one or more organs (target organ classes) which correspond to the areas of the one or more organs in the X-ray images, wherein the boundary of a target organ class in an X-ray image corresponds to the boundary of a corresponding organ in the X-ray image. Additionally, in some embodiments the SCAN framework 200 also trains a critic network with an input mask, such as 212 or 214, wherein the input mask is one of a segmentation network mask and a ground truth annotation, and outputting a probability that the input mask is the ground truth annotation instead of the prediction by the segmentation network. In some embodiments, methods of organ segmentation may be used in medical imaging scans other than chest X-rays, for example, in medical images that have similar aspects such as two-dimensional projections of three-dimensional structures.

In this embodiment, SCAN framework 200 then provides the probability output by the critic network 400 to the segmentation network 300 to guide the segmentation network 300 to generate masks more consistent with learned higher-order structures.

In some embodiments, SCAN framework 200 may further comprise training the segmentation network 300 by minimizing a loss function of the segmentation network, and training the critic network by minimizing a loss function of the critic network, for example, as shown above with loss functions $$\sum_{i=1}^{N} J_d(D(x_i, y_i), 1) +$$

$J_d(D(x_i, S(X_i)), 0)$ and $\sum_{i=1}^{N} J_s(S(x_i), y_i) + \lambda J_d(D(x_i, S(x_i)), 1),$ for the critic network and segmentation network, respectively. By way of example, the loss function of the segmentation network 300 may be a multi-class cross-entropy loss for predicted segmentation network mask averaged over all pixels and the loss function of the critic network 300 is a binary logistic loss for the critic networks prediction. Other embodiments are not limited to these loss functions but may otherwise utilize a critic network adversarially to a segmentation network.

In some embodiments, training a segmentation network 300 by minimizing a loss function of the segmentation network and training a critic network 400 by minimizing a loss function of the critic network, may further include alternating between optimizing the segmentation network and the critic network using their respective loss functions to segment lung fields and the heart in a chest X-ray image, for example, as with Eq. (1) above. In some embodiments, the segmentation network 300 is a fully convolutional neural network and include a down-sampling path including convolutional layers and pooling layers, and an up-sampling path including convolutional layers and transposed convolutional layers to predict scores for each class at a pixel level using an output of the down-sampling path.

Figure 5:
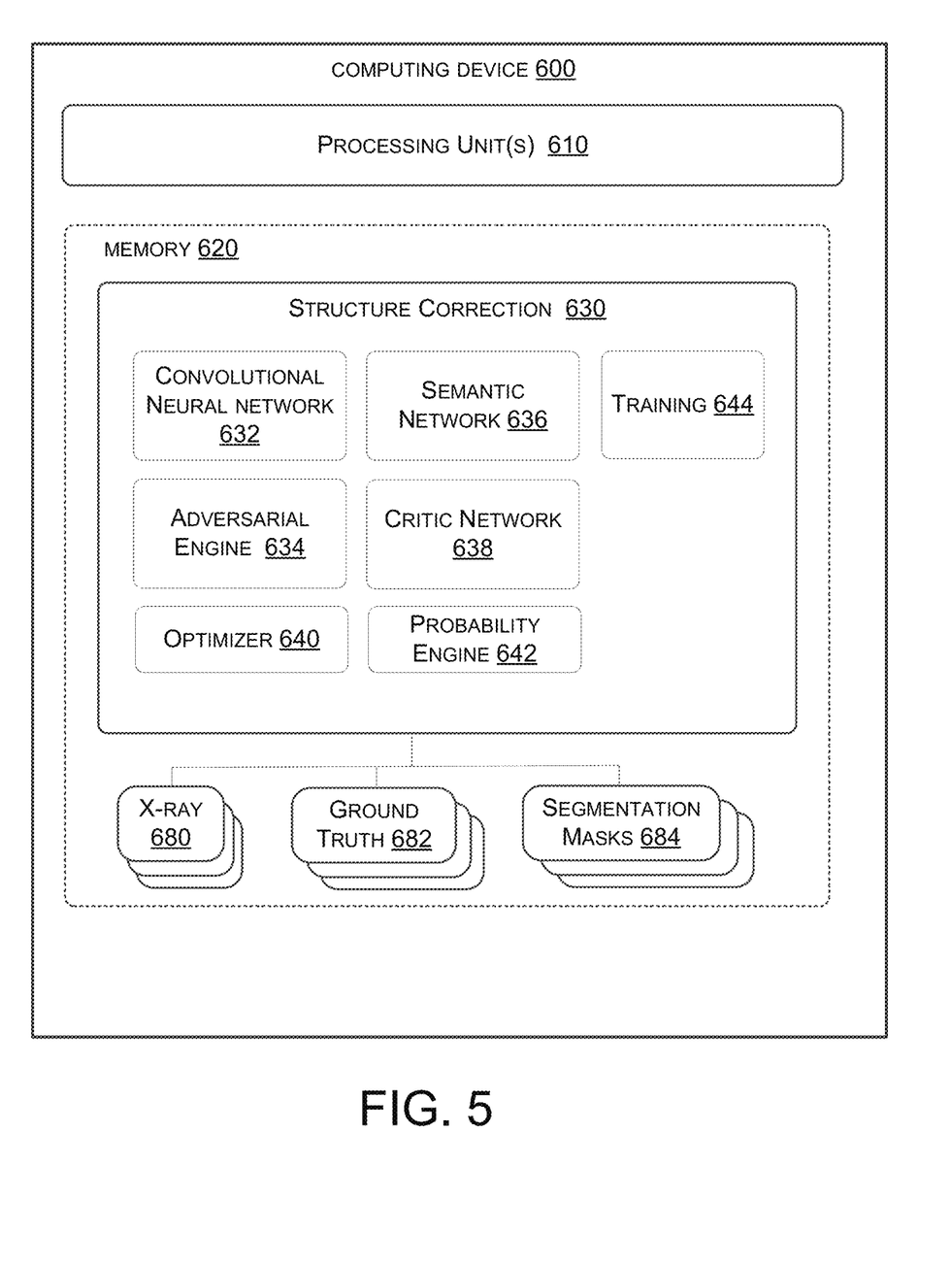
FIG. 5 shows one example embodiment SCAN framework computing device.

FIG. 5 shows one example embodiment SCAN framework computing device 600, including one or more processing units 610, memory 620 and resident in memory a structure correction module 630 and X-ray images 680, ground truth masks 682 and segmentation masks 684. Structure correction module includes a convolutional neural network module/engine 632, an adversarial engine 634, an optimizer 640, a probability engine 642, and a training block 644.

In the embodiment in FIG. 5, a structure correction engine 630 includes a semantic network module 636 and a critic network module 638, where the structure correction engine 630 may further have stored in memory a set of input chest X-ray images having a height dimension and a width dimension and having stored in memory a set of mask labels having a height dimension, a width dimension, and a plurality of classes. Upon receiving X-ray images 680 into structure correction module 630, the semantic network module 636 may calculate class probabilities of the input chest X-ray images depicted by a segmentation network for each of a plurality of pixel locations. In some embodiments, the organ segmentation may be generated without the critic network module 638 and only using the semantic network module. In some embodiments, the critic network module 638 may then generate a scalar probability estimate using at least one of the set of mask labels in a critic network.

Training module 644 trains a segmentation network by minimizing a loss function of the segmentation network and to train a critic network by minimizing a loss function of the critic network, as referenced above, and adversarial engine 634 alternates between optimizing the segmentation network and the critic network using their respective loss functions to segment lung fields and the heart in a chest X-ray image. In some embodiments, the adversarial training module may discriminate between ground truth annotations 682 and the segmentation network predicted class probabilities 684 in training the segmentation network.

While various embodiments of the invention have been described above, they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, the various features and functionality described in one or more of the individual embodiments are not limited in their applicability to the particular embodiment with which they are described. They instead can be applied alone or in some combination, to one or more of the other embodiments of the disclosure, whether or not such embodiments are described, and if such features are presented as being a part of a described embodiment. Thus, the breadth and scope of the present disclosure should not be limited by any of the above-described exemplary embodiments.

In this document, the terms "module" and "engine" as used herein, refers to software, firmware, hardware, and any combination of these elements for performing the associated functions described herein. Additionally, for purpose of discussion, the various modules are described as discrete modules; however, as would be apparent to one of ordinary skill in the art, two or more modules may be combined to form a single module that performs the associated functions according embodiments of the invention.

In this document, the terms "computer program product", "computer-readable medium", and the like, may be used generally to refer to media such as, memory storage devices, or storage unit. These, and other forms of computer-readable media, may be involved in storing one or more instructions for use by processor to cause the processor to perform specified operations. Such instructions, generally referred to as "computer program code" (which may be grouped in the form of computer programs or other groupings), when executed, enable the computing system.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be references to suitable means for providing the described functionality, rather than indicative of a strict logical or physical structure or organization.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to", or other like phrases in some instances shall not be read to mean that the narrower case is intended or required in instances where such broadening phrases may be absent.

Additionally, memory or other storage, as well as communication components, may be employed in embodiments of the invention. It will be appreciated that, for clarity purposes, the above description has described embodiments of the invention with reference to different functional units and processors. However, it will be apparent that any suitable distribution of functionality between different functional units, processing logic elements or domains may be used without detracting from the invention. For example, functionality illustrated to be performed by separate processing logic elements or controllers may be performed by the same processing logic element or controller. Hence, references to specific functional units are only to be seen as references to suitable means for providing the described functionality, rather than indicative of a strict logical or physical structure or organization.

Furthermore, although individually listed, a plurality of means, elements or method steps may be implemented by, for example, a single unit or processing logic element. Additionally, although individual features may be included in different claims, these may possibly be advantageously combined. The inclusion in different claims does not imply that a combination of features is not feasible and/or advantageous. Also, the inclusion of a feature in one category of claims does not imply a limitation to this category, but rather the feature may be equally applicable to other claim categories, as appropriate.

The invention claimed is:

1. Enacted on a computing device to segment organs in a chest X-ray image, a method comprising: training a segmentation network with chest X-ray images;
    further training the segmentation network by minimizing a loss function of the segmentation network, and
    generating pixel-level predictions of target classes, wherein the target classes include classes for one or more organs (target organ classes) which correspond to the areas of the one or more organs in the X-ray images, wherein the boundary of a target organ class in an X-ray image corresponds to the boundary of a corresponding organ in the X-ray image;
    training a critic network with an input mask, wherein the input mask is one of a segmentation network mask and a ground truth annotation, and outputting a probability that the input mask is the ground truth annotation instead of the prediction by the segmentation network, wherein the critic network is trained by minimizing a loss function of the critic network; and
    providing the probability output by the critic network to the segmentation network to guide the segmentation network to generate masks more consistent with learned higher-order structures.

2. The method of claim 1, wherein the loss function of the segmentation network is a multi-class cross-entropy loss for predicted seg en ation network mask averaged over all pixels.

3. The method of claim 1, wherein the loss function of the critic network is a binary logistic loss for the critic networks prediction.

4. The method of claim 1, wherein training a segmentation network by minimizing a loss function of the segmentation network and training a critic network by minimizing a loss function of the critic network, further comprises alternating between optimizing the segmentation network and the critic network using their respective loss functions to segment lung fields and the heart a chest X-ray image.

5. The method of claim 1, wherein the segmentation network is a fully convolutional neural network, further comprising:
   a down-sampling path including convolutional layers and pooling layers; and
   an up-sampling path including convolutional layers and transposed convolutional layers to predict scores for each class at a pixel level using an output of the down-sampling path.

6. The method of claim 1, wherein training a critic network with an input mask, wherein the input mask is one of a segmentation network mask and a ground truth annotation, further comprises training the critic network with a chest X-ray image.

* * * * *